United States Patent
Hu

(10) Patent No.: US 9,241,936 B2
(45) Date of Patent: Jan. 26, 2016

(54) USE OF RUPATADINE IN THE MANUFACTURE OF PHARMACEUTICAL COMPOSITION FOR TREATING CHRONIC OBSTRUCTIVE PULMONARY DISEASE

(75) Inventor: Zhuowei Hu, Beijing (CN)

(73) Assignee: BEIJING WEIFENG YIMIN BIO-TECHNOLOGY LIMITED COMPANY (CN)

( * ) Notice: Subject to any disclaimer, the term of this patent is extended or adjusted under 35 U.S.C. 154(b) by 0 days.

(21) Appl. No.: 14/383,459

(22) PCT Filed: May 18, 2012

(86) PCT No.: PCT/CN2012/075729
§ 371 (c)(1),
(2), (4) Date: Sep. 5, 2014

(87) PCT Pub. No.: WO2013/131324
PCT Pub. Date: Sep. 12, 2013

(65) Prior Publication Data
US 2015/0018382 A1 Jan. 15, 2015

(30) Foreign Application Priority Data

Mar. 6, 2012 (CN) .......................... 2012 1 0058649

(51) Int. Cl.
| | | |
|---|---|---|
| A61K 31/56 | (2006.01) | |
| A61K 31/4545 | (2006.01) | |
| A61K 45/06 | (2006.01) | |

(52) U.S. Cl.
CPC ............. *A61K 31/4545* (2013.01); *A61K 45/06* (2013.01)

(58) Field of Classification Search
USPC .................................. 514/290, 168, 560, 547
See application file for complete search history.

(56) References Cited

U.S. PATENT DOCUMENTS

| 7,799,782 B2 * | 9/2010 | Munson et al. ............ 514/234.5 |
| 2009/0324699 A1 * | 12/2009 | Preswetoff-Morath et al. ............................. 424/450 |

FOREIGN PATENT DOCUMENTS

| CN | 101257891 A | 9/2008 |
| CN | 101 669 926 A | 3/2010 |
| CN | 102 145 002 A | 8/2011 |
| CN | 102145002 A | 11/2011 |
| CN | 102614177 A | 1/2012 |
| EP | 2823818 A1 | 1/2015 |
| WO | WO 2007/026151 A1 | 3/2007 |
| WO | 2010/054158 | 5/2010 |
| WO | 2010/075090 | 7/2010 |

OTHER PUBLICATIONS

Dec. 27, 2012 Written Opinion of the International Searching Authority issued in International Patent Application No. PCT/CN2012/075729.
Feb. 5, 2013 Chinese 1st Office Action issued in Chinese Patent Application No. 201210058649.X.
Sep. 23, 2013 Chinese 2nd Office Action issued in Chinese Patent Application No. 201210058649.X.
International Search Report dated Dec. 27, 2012 from PCT/CN2012/075729.
Gronke et al. "Effect of cetirizine dihydrochloride on the airway response to hypertonic saline aerosol in patients with chronic obstructive pulmonary disease (COPD)" Respiratory Medicine. Bailliere Tindall. London. GB. vol. 99, No. 10, Oct. 1, 2005 pp. 1241-1248.
Graul A. I. "Respiratory Drug Development Compendium 2002 Allergic Rhinitis" Drugs of the Future. Prous Science. ES. vol. 27, No. 12, Dec. 1, 2002 pp. 1181-1194.
Extended European Search Report dated Jul. 29, 2015, from European Patent Application No. 12870905.2, 7 pages.
Zhang, X., et al. "Toll-like receptor 4 deficiency causes pulmonary emphysema" The Journal of Clinical Investigation, http://www.jci.org, Nov. 2006, vol. 116, No. 11, pp. 3050-3059.
Marmouz, F., et al. "Morning and evening efficacy evaluation of rupatadine (10 and 20 mg), compared with cetirizine 10 mg in perennial allergic rhinitis: a randomized, double-blind, placebo-controlled trial" Journal of Asthma and Allergy, 2011, vol. 4, pp. 27-35.

* cited by examiner

*Primary Examiner* — Rei-Tsang Shiao
(74) *Attorney, Agent, or Firm* — Quarles & Brady LLP

(57) ABSTRACT

Disclosed is the use of rupatadine in the manufacture of pharmaceutical composition for preventing or treating chronic obstructive bronchitis, obstructive emphysema or chronic obstructive pulmonary disease. The new medicament, i.e. rupatadine, for treating chronic obstructive pulmonary disease is obvious in therapeutic effects, and low in toxic and side effects, and safe in use in the aspects of treating chronic obstructive bronchitis, obstructive emphysema or chronic obstructive pulmonary disease.

15 Claims, 2 Drawing Sheets

USE OF RUPATADINE IN THE MANUFACTURE OF PHARMACEUTICAL COMPOSITION FOR TREATING CHRONIC OBSTRUCTIVE PULMONARY DISEASE

FIELD OF THE INVENTION

The present invention relates to use of rupatadine in the manufacture of pharmaceutical composition for treating chronic obstructive pulmonary disease.

PRIOR ARTS

Chronic obstructive pulmonary disease (COPD) is a disease characterized by airflow limitation. It is usually in progressive course and cannot be totally converted, which is mostly related to abnormal inflammatory response of lung to harmful particle or gas, with the features like breath airflow decline and lung emptying tardiness. The clinical features of COPD include asthma, cough and expectoration accompanied by chronic airway obstruction and lung over-expansion. During the attack, chronic bronchitis and emphysema happen at the same time. Airway remolding of COPD may cause the functional change of airway, including successive inconvertible narrow of airway and the over-secretion of mucus. Mainly caused by smoking, COPD has relatively high morbidity and lethal rate while the present therapeutic effects are very limited. The statistics of WHO indicates that COPD was the disease with the sixth highest lethal rate in 1990 and will be the third in 2020 in anticipation.

Smoking is a primary factor leading COPD, the majority of COPD patients have long smoking experiences, and age is another important factor leading COPD. The paroxysm of COPD is of a long period and has unobvious signs. Usually, the acute attack of bronchitis is not diagnosed as COPD, and clinical patients will have different features of disease. As a result, it is difficult to make accurate diagnose of COPD in the early phase, and most patients will not seek for medical help until their lung functions decrease or have other symptoms such as breath difficulty and successive cough and expectoration. Thus, the diagnose of COPD is usually made in the middle or severe phase. As COPD is usually accompanied by emphysema and chronic bronchitis, the therapy becomes more difficult. The present clinical medicaments belong to conservative therapy which cannot make pathologic changes fundamentally.

Rupatadine, CAS number 158876-82-5 has a molecular formula as $C_{26}H_{26}ClN_3$, molecular weight as 415.958, a protein combination rate as 98-99%, and a half-life period as 5.9 hours. Its structure is shown as formula I.

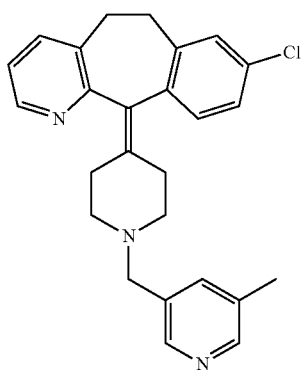

Formula 1

Rupatadine is a new anti-allergy medicament produced by Uriach, a Spanish pharmaceutical company, and came into the market in Spain for the first time on Mar. 15, 2003 for treating seasonal and perennial anaphylactic rhinitis. The commercial name is Rupafin and Dupafin and dosage is 10 mg once a day.

Rupatadine has a bi-function of anti-histamine and anti-platelet activating factor (PAF). Researches show that allergy and inflammatory diseases are multi-factor complex process generated by the production and release of various different mediators. Histamine is the most inflammatory mediators found at the early allergy phase and when the symptoms of this kind of diseases appear, existing in mastocyte and basophilic granulocyte. The mastocyte and basophilic granulocyte activated by allergen will produce and release histamine, which can promote the shrink of smooth muscle, the expansion of blood vessel, enhance the permeability of blood capillary as well as the secretion of mucosal glands, and induce type I hypersensitivity. Therein, the symptoms of sneezing, rhinocnesmus, tearing, nasal discharge are mostly induced by histamine H1 receptors. PAF is another important inflammatory mediators of airway inflammation. Similarly to histamine, PAF can cause shrink of bronchus and enhance the permeability of blood vessels, which leads to nasal discharge and nasal congestion. Meanwhile, PAF can also enhance the sensitivity of bronchus, which is the main inducing factor of asthma. It is indicated by researches that 66% of asthma is induced by rhinitis, and nasal diseases are the beginning of weasand diseases such as asthma, chronic obstructive pulmonary disease, and bronchiectasia etc. Latest research of PAF functional mechanism shows that PAF acts on airway indirectly leading to obstruction and high sensitivity hyperfunction and further inducing the release of leukotrienes. PAF is complementary to histamine in general. Histamine is an early response media released by containers of mastocytes, while PAF is de novo synthesized. However, currently, the clinical anti-allergy medicament has only anti-histamine activity rather than anti-PAF activity. It is obvious that a medicament with both anti-histamine and anti-PAF activity will have better clinical performance than that with only one. Rupatadine is the only commercial available anti-allergy medicament with both anti-histamine and anti-PAF activity presently, so it has promising prospective in clinical application.

Rupatadine has good affinity to histamine H1 receptors. Induced by the anti-histamine activity of rupatadine, the ileum of Guinea pig can be shrinked in vitro. According to this, the comparison of rupatadine and the first and second generation of anti-histamine medicaments in the prior art shows: rupatadine has stronger anti-histamine activity than terfenadine, loratadine, cetirizine, hydroxyzine, diphenhydramine. Herein, the anti-histamine activity of rupatadine (IC50=0.0035 μm) is 80 times stronger than that of loratadine (IC50=0.29 μm), and 100 times stronger than that of other anti-histamine medicaments. The anti-histamine activity of rupatadine is the same as desloratadine in vitro. In addition, experiments in vitro show some metabolin of rupatadine also have anti-histamine activity, and the anti-histamine activity of some specific metabolin is at the same level with desloratadine, the metabolin of loratadine.

In prior art, the researches of anti-PAF activity of rupatadine is conducted on models of several animals such as mouse, rabbit, Guinea pig and dog both in vivo and in vitro. In the experiment of platelet aggregation induced by anti-PAF activity, IC50 of rupatadine in platelet rich plasma, serum of rabbits and whole blood of dogs are 2.9, 0.2 and 0.29 μm respectively. This experiment shows that rupatadine has good PAF antagonism. However, the experiment of platelet aggregation induced by PAF antagonism in platelet-rich plasma of rabbits shows that IC50 of the second generation of anti-histamine medicaments, such as loratadine, cetirizine, mizolastine, fexofenadine are 7142, 7200, 7200 and 7200 μm respectively, suggesting little or very weak PAF antagonism. In the model of blister induced by subcutaneous injecting histamine or PAF in dogs, rupatadine can effectively inhibit blister (0.3-10 mg/kg, oral administration), while loratadine and cetirizine can only inhibit the blister induced by histamine. The best potency will appear in 4 hours after intake of rupatadine and the effect will last for 24 hours, suggesting rupatadine is a sustained-release medicament. Rupatadine can inhibit conjunctivitis induced by histamine or PAF of Guinea pig, while loratadine cannot inhibit the conjunctivitis induced by PAF. If rupatadine is applied to eye drops, the therapy effect will be 10 times better than that of loratadine.

In addition, compared to other anti-histamine medicaments, rupaladine shows broader-spectrum pharmacological activity in non-histamine-dependent pharmacological models. It can inhibit the degranulation of mastocytes as well as the chemotaxis of eosinophil. The degranulation of mastocytes plays an important role in allergy process, especially in the early phase, while eosinophil is the key response cell in the later phase of allergy. The oral administration of rupatadine is absorbed fast and with a half-life period of 12 hours, in general, the blood concentration will reach the peak after intaking tablet in 1 hour, while will reach the peak after intaking the capsule in 1.5 hours. Rupatadine metabolizes through liver and gall primarily. Some of the metabolin also have anti-histamine activity, which may make rupatadine have systemic and long-effective anti-allergy activity.

The II and III phases of clinical experiments of rupatadine were done in 10 clinical experiment centers in Spain, France, South Africa, United Kingdom and more than 2900 patients, aged from 12 to 82 and suffering seasonal or perennial allergic rhinitis, took participate into the experiments. The safety and effectiveness of rupatadine have been affirmed through experiments. Experiments evaluating the safety and effectiveness in two weeks with feeding rupatadine 2.5 mg, 5 mg, 10 mg, 20 mg per day were carried out relative to placebo. The results show that rupatadine can alleviate the symptoms more effectively than placebo, among them, feeding 20 mg per day got the highest score in symptom alleviation and 10 mg per day had the best comprehensive therapy effects. Another experiment evaluating the safety and effectiveness of rupatadine with feeding 10 mg and 20 mg per day for patients suffering seasonal allergic rhinitis relative to placebo: the patients are divided into three groups, i.e. 10 mg group. 20 mg group and placebo group, at random. The medicaments were taken every day for two weeks, the results show that nasal and optical symptoms for seasonal allergic rhinitis patients were much more alleviated by intaking of 10 mg and 20 mg per day rupatadine than placebo. Hereinto, intaking 10 mg per day has no significant difference to 20 mg per day, while intaking 20 mg per day will have a better alleviation trend in a week.

Further, comparing rupatadine to other anti-histamine medicaments, it is shown that 10 mg per day rupatadine has similar effects with the same dosage of cetirizine, while the former has little side effects on central nervous system. And rupatadine can alleviate the symptoms of seasonal allergic rhinitis more than loratadine and ebastine under the same dosage.

In a random, double-blind, placebo controlled, multicenter parallelled intake test, comparing intaking 10 mg or 20 mg per day rupatadine, 10 mg per day loratadine or placebo for two weeks for treating patients suffering seasonal allergic rhinitis, the results showed that intaking 10 mg or 20 mg per day rupatadine had better effects than intaking 10 mg per day loratadine and specially in alleviating symptoms of sneezing and rhinocnesmus.

In another random, double-blind, placebo controlled, multicenter parallelled intake test, 250 patients with seasonal allergic rhinitis took 10 mg rupatadine, 10 mg ebastine or placebo daily for 2 weeks. The results showed that rupatadine had better therapeutic effects than ebastine, especially in alleviating sneezing and tearing, the former was far better than the latter.

Rupatadine is highly selective to peripheral nervous receptors H1 and has strong and long-lasting activity, while its affinity to central nervous system is little and has little permeability of blood brain barrier, so there is no side effect of calm. The experiments showed that even if 1000 mg/Kg and 10 mg/Kg of rupatadine were given to a mouse and macaque respectively, the period of QTC and QRS would not be extended, nor would it lead to arrhythmia in rats, Guinea pigs and dogs. Also 3-hydroxy desloratadine, the main metabolin of rupatadine in vivo does not affect cardiomotility, perhaps due to the little concentration of rupatadine in heart and it is usually difficult to be detected. As a result, rupatadine will not cause cardiotoxicity and no accumulation reaction will occur after successive intaking. It also has no effect on alcohol, a wide range of safe dosage and good tolerance.

The latest research shows that rupatadine has good ability against pulmonary fibrosis, and it also can convert the pulmonary fibrosis induced by Bleomycin, declining the lethal rate caused by pulmonary fibrosis induced by Bleomycin of mammals. Rupatadine can decline the inflammation and EMT in tissues of pulmonary fibrosis, and also the deposition of collagen, enhance the lung function.

Distinguished from pulmonary fibrosis, COPD has its own unique causes and process. So the medicaments against pulmonary fibrosis may not be used in treating COPD. Although smoking and aging are the most common causes for COPD, there are still proofs that non-smoking and non-elderly people can also suffer COPD. So the nosogenesis of COPD is so complicated that basic pulmonary inflammation theory or other academic theories in present cannot cover it.

Nowadays, there still lacks effective therapy for chronic obstructive pulmonary disease, as a result, it is urgent to develop a new medicament with good therapeutic effects in alleviating or treating COPD.

CONTENT OF THE PRESENT INVENTION

The technical problem to be solved in the present invention is, regarding the lack of drugs for preventing or treating chronic obstructive pulmonary disease, to provide a new use of rupatadine. Rupatadine can be used for effectively preventing or treating chronic obstructive bronchitis, obstructive emphysema or chronic obstructive pulmonary disease.

The technical solution adopted to solve the technical problem above is that a use of rupatadine in the manufacture of pharmaceutical composition for preventing or treating chronic obstructive bronchitis, obstructive emphysema or chronic obstructive pulmonary disease.

In the present invention, the "chronic obstructive bronchitis" means chronic, non-specific inflammation of tracheal and bronchial mucosa and surrounding tissues thereof, which is clinically characterized by cough, expectoration or a chronic process accompanied by gasp and repeated attacks.

In the present invention, the "obstructive emphysema" is caused by the narrow of bronchiole resulted by chronic bronchitis or other reasons, over-gassing of far-ending air cavity of bronchioli terminales accompanied by expansion or explosion of air cavity wall, and it is usually the complication of chronic bronchitis in clinical.

In the present invention, the "chronic obstructive pulmonary disease" (COPD) is a disease characterized by the limitation of airflow. The clinical symptoms thereof include the decline of breath airflow, the tardiness of lung emptying, asthma, cough, expectoration, accompanying by the chronic obstructive of air passage and the over expansion of lung, as well as experiencing chronic obstructive bronchitis and obstructive emphysema during an attack.

In the present invention, the chronic obstructive pulmonary disease is the COPD of human beings or animals.

In the present invention, the "preventing" is to prevent or decline the occurrence of chronic obstructive bronchitis, obstructive emphysema or COPD in the presence of possible factors of chronic obstructive bronchitis, obstructive emphysema or COPD.

In the present invention, the "treating" is to alleviate the degree of chronic obstructive bronchitis, obstructive emphysema or COPD, or to cure and normalize chronic obstructive bronchitis, obstructive emphysema or COPD, or to decelerate the process of chronic obstructive bronchitis, obstructive emphysema or COPD. Specifically, rupatadine can improve the lung function effectively, recover the basic physiological structure of lung, decline the infiltration and expression of various inflammatory cells, decline the degree of inflammation and infiltration of inflammatory cells. Rupatadine plays a role in adjusting body immune balance in chronic pulmonary diseases, and balances the immune reaction between Th1 and Th2. Rupatadine can convert COPD and treat asthma, improve the lung function and convert emphysema.

In the present invention, the "rupatadine" is rupatadine or the pharmaceutical acceptable derivative thereof, including pharmaceutical acceptable salt, ester and so on.

In the present invention, the pharmaceutical composition preferably comprises rupatadine and pharmaceutical carrier.

Therein, the pharmaceutical composition more preferably comprises 0.1%-99% rupatadine and 0.1%-99% pharmaceutical carrier, the percentage is a mass percentage of each component to the total mass of the pharmaceutical composition.

Therein, rupatadine can be active ingredient individually or together with other compounds. The "active ingredient" is an active ingredient with activity in treating chronic obstructive bronchitis, obstructive emphysema or chronic obstructive pulmonary disease.

Therein, the pharmaceutical composition preferably comprises inhibitors against histamine 1-4 receptors and/or an inhibitor against PAF receptor.

Therein, the pharmaceutical carrier comprises pharmaceutical acceptable excipient, filler and diluent etc.

Therein, there is no special limitation in formulation of the pharmaceutical composition. It can be solid, semisolid or liquid, it can also be an aqueous solution, a non-aqueous solution, or a suspension. It can be a pill, a capsule, particle, an injection, or an infusion agent etc. as well. The pharmaceutical composition can be administered orally, intravenously, intramuscularly, intradermally or hypodermically.

Dosage of the pharmaceutical composition containing rupatadine in the present invention depends on the age and state of illness of patients. The daily dosage is about 0.0001-1000 mg in general, preferably 0.01-500 mg, more preferably 0.1-200 mg. The pharmaceutical composition is given once or more than once a day.

In the process of preventing or treating COPD, the pharmaceutical composition containing rupatadine can be used alone or together with other medicaments.

Unless otherwise indicated, the reagents and raw materials used in the present invention are all commercially available.

In the present invention, the mentioned optimized conditions can be optionally combined based on the general knowledge in this field to obtain preferred embodiments.

The positive effects of the present invention are as follows: the present invention provides a new medicament-rupatadine for preventing or treating. It has significant therapeutic effects in treating chronic obstructive bronchitis, obstructive emphysema or chronic obstructive pulmonary disease with low toxicity and little side effects, and is safe in use.

DETAILED DESCRIPTION OF THE PREFERRED EMBODIMENT

The following examples further illustrate the present invention, but the present invention is not limited thereto.

In the following embodiments, "%" in solutions represents quality volume percent. Results of experiments are expressed in the form of average±standard error (X±SE), and examined by the parameter or non-parameter variance. After comparison, $p<0.05$ is regarded as having significant difference, $p<0.01$ is regarded as having extremely significant difference. Chi-square test is used in the statistics of pathology classification information. After comparison, $p<0.05$ is regarded as having significant difference, and $p<0.01$ is regarded as having extremely significant difference. PBS (i.e. phosphate buffer solution) used in the embodiments has a concentration of 0.1M and pH value of 7.2.

Embodiment 1

1. The Preparation of COPD Animal Model

Main agents and animals for experiments: Cigarettes used in the experiment, type 3R4F, were purchased from Tobacco Research Center, University of Kentucky, USA. C57BL/6 mice on level SPF used in the experiment (male, aged 6-8 weeks, 16-18 g) were purchased from Institute of Animal, Chinese academy of medical sciences.

Preparation of COPD animal model: C57BL/6 mice were put in a smoke box and 5 cigarettes were inhaled without filter tip each time. The ratio of smoke to air was 1:6, and the whole flow rate of gas was 150 ml/min. Smoking experiment was conducted 4 times a day, 30 minutes for each time and last for 24 weeks.

2. Treating COPD of Smoking Mice by Rupatadine

Main agents: rupatadine, produced by Zhejiang Cifu pharmaceutical limited company. It is the API of rupatadine fumarate. The content of rupatadine is more than 99%.

Therapy: grouping and feeding animal models with medicaments. The groups were as table 1:

TABLE 1

| Number | Group | The number of animals | Dosage and drug regimen | Route of administration | Solvent |
|---|---|---|---|---|---|
| A | Sham | 15 | Equivalent amount of solvent, lasting for 4 weeks after modeling, once a day | i.g. | PBS |
| B | Model | 20 | Equivalent amount of solvent, lasting for 4 weeks after modeling, once a day | i.g. | PBS |
| C | Rupa | 20 | 6 mg/kg rupatadine, lasting for 4 weeks after modeling, once a day | i.g. | PBS |

Note:
Group A is sham-operation group (Sham). Group B is model group (Model), and group C is rupatadine treated group (Rupa).

3. Test the Amount of Inflammatory Cells in Bronchoalveolar Lavage Fluid of COPD Mice The mice were dissected at neck and the weasand was exposed for intubation. The lavage amount of PBS was 0.8 ml and the lavage was conducted 3-5 times. The lavage solution was recycled and centrifuged at 1500 r for 10 minutes at 4° C. The supernate was recycled and kept at −20° C. for the test of cytokines.

Figure 1:
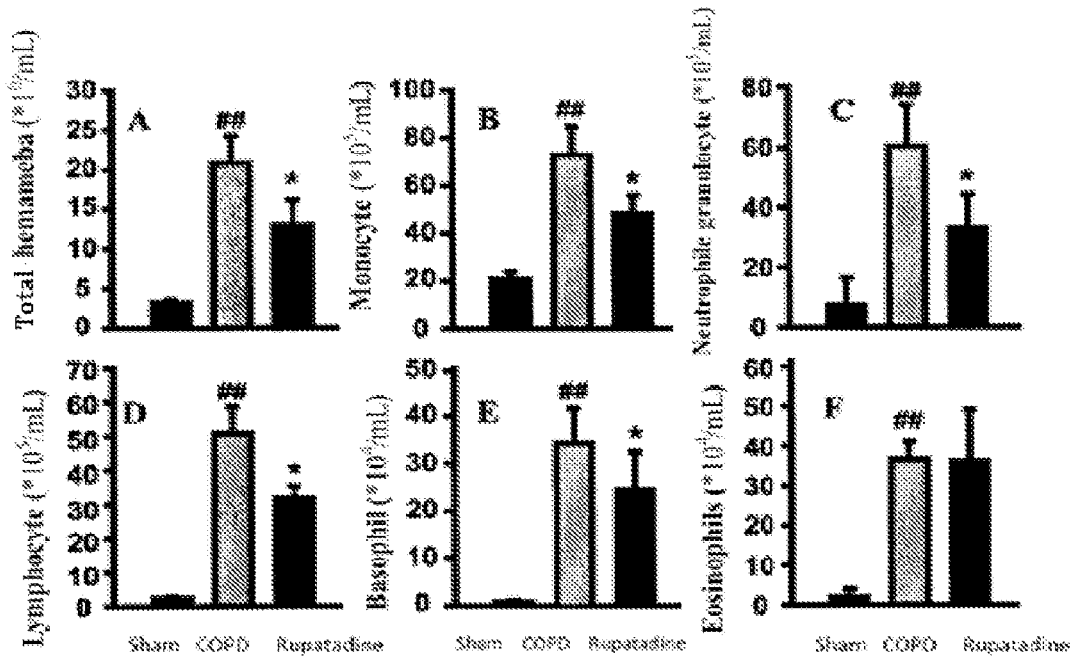
FIG. 1 is a contrast figure about the amount of various inflammatory cells in bronchoalveolar lavage fluid of sham-operation group, model group and rupatadine treated group of smoking-induced COPD mice in embodiment 1.

Cells were reselected and precipitated by 1 ml 1% BSA in PBS. 10 μl resuspension solution was taken for calculating the amount of cells and the hematology analyzer was used for analysis. The results were shown in FIG. 1, and the detailed data were shown in Table 2. It can be seen from FIG. 1, compared with the sham-operation group, the total number of hemameba (FIG. 1A), monocyte (FIG. 1B), neutrophile granulocyte (FIG. 1C), lymphocyte (FIG. 1D), basophil (FIG. 1E), and eosinophils (FIG. 1F) in bronchoalveolar lavage fluid of smoking-induced COPD mice increased extremely remarkably. So it indicated that 6 mg/kg rupatadine treated group could remarkably reduce the amount of various inflammatory cells in bronchoalveolar lavage fluid of smoking-induced COPD mice compared to the model group.

TABLE 2

| Group | total hemameba (number/mL) | Monocyte (number/mL) | Neutrophile granulocyte (number/mL) | Lymphocyte (number/mL) | Basophil (number/mL) | Eosinophils (number/mL) |
|---|---|---|---|---|---|---|
| Sham | $3.874 * 10^6$ | $21.731 * 10^5$ | $8.138 * 10^5$ | $3.767 * 10^5$ | $2.082 * 10^4$ | $1.979 * 10^4$ |
| Model | $21.266 * 10^6$ | $72.086 * 10^5$ | $60.259 * 10^5$ | $51.945 * 10^5$ | $33.791 * 10^4$ | $37.084 * 10^4$ |
| Rupa | $13.69 * 10^6$ | $49.504 * 10^5$ | $33.864 * 10^5$ | $32.694 * 10^5$ | $24.816 * 10^4$ | $34.692 * 10^4$ |

4. Test the Amount of Inflammatory Cytokines in Bronchoalveolar Lavage Fluid of COPD Mice The mice were dissected at neck and the weasand was exposed for intubation. The lavage amount of PBS was 0.8 ml and the lavage was conducted 3-5 times. The lavage solution was recycled and centrifuged at 1500 r for 10 minutes at 4° C. The supernate was recycled and kept at −20° C. for the test.

Figure 2:
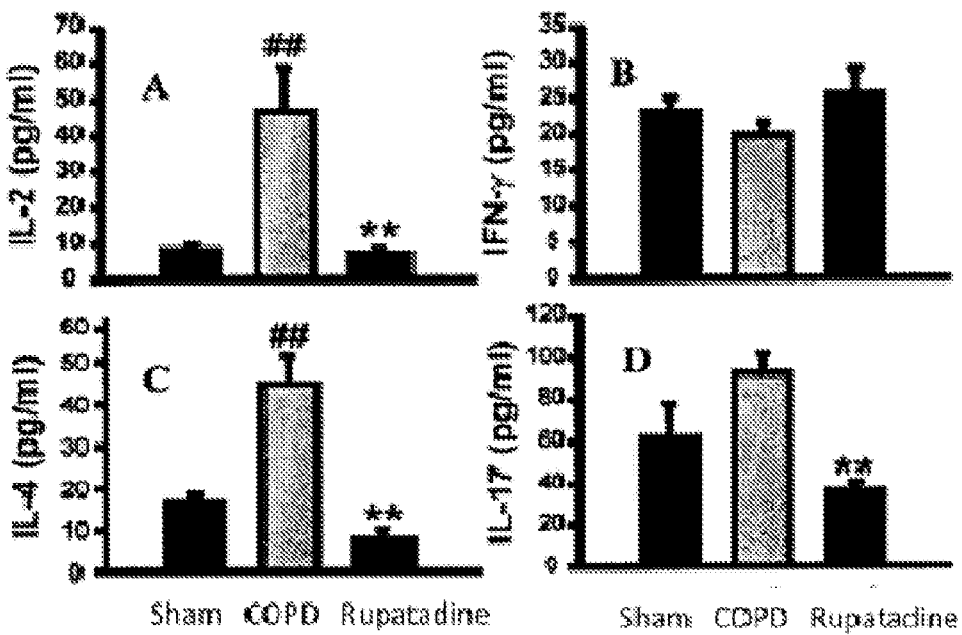
FIG. 2 is a contrast figure about the amount of various inflammatory cytokines in bronchoalveolar lavage fluid of sham-operation group, model group and rupatadine treated group of smoking-induced COPD mice in embodiment 1.

100 μl supernate was taken to conduct ELISA examination, and commercial available ELISA kit was used to test the amount of inflammatory cytokines. The results were shown in FIG. 2, and the detailed data were shown in Table 3. It can be seen from FIG. 2, compared with the sham-operation group, the content of IL-2 (FIG. 2A), IL-4 (FIG. 2C), IL-17 (FIG. 2D) increased remarkably in lungs of COPD mice. It indicated that 6 mg/Kg rupatadine treated group could reduce the content of various inflammatory cytokines in lungs of COPD mice, while rupatadine did not affect the content of IFN-γ (FIG. 2B), which plays an important role in tissue repair. So it was proved that rupatadine can adjust body immune reactions directionality.

TABLE 3

| Group | IL-2 | IFN-γ | IL-4 | IL-17 |
|---|---|---|---|---|
| Sham | 8.85 pg/ml | 22.17 pg/ml | 18.33 pg/ml | 61.63 pg/ml |
| Model | 46.79 pg/ml | 19.65 pg/ml | 45.2 pg/ml | 92.48 pg/ml |
| Rupa | 6.71 pg/ml | 26.28 pg/ml | 6.54 pg/ml | 35.53 pg/ml |

5. Pathological Evaluation of Smoking-Induced COPD Mice

HE staining method is also named Hematoxylin-Eosin staining method. Hematoxylin dye liquor is alkaline, and mainly colors intranuclear chromatin and intracytoplasmic ribosome into bluish violet. Eosin is acidic dye, and mainly colors the components in cytoplasm and extracellular matrix.

Figure 3:
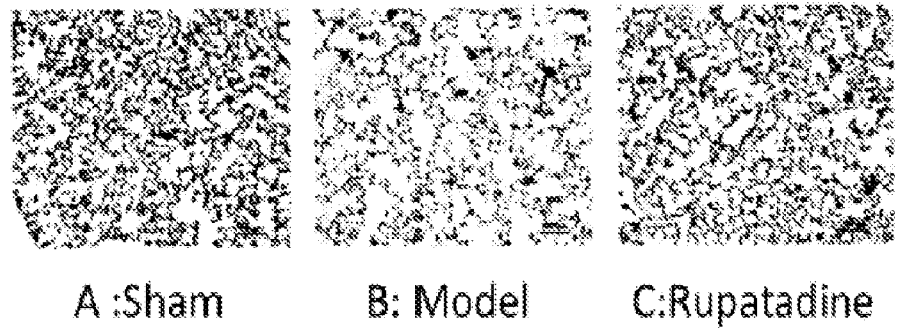
FIG. 3 shows pathological examination photos of lung tissue of sham-operation group, model group and rupatadine treated group of smoking-induced COPD mice in embodiment 1.

The lung tissues on the right lower lobe was cut, fixed by 4 wt % paraformaldehyde and then embedded by paraffin. The largest cross-section of the paraffin embedding lung tissue was stained by HE staining method, and the result was shown in FIG. 3. FIG. 3 showed that the area of alveoli increased remarkably in the lungs of COPD mice (FIG. 3B), and the far-end air cavity of terminal bronchiole was expanded, the normal lung tissue was destroyed with the occurrence of emphysema, while rupatadine could effectively recover normal structure of alveoli (FIG. 3C), and decrease the expansion of far-end air cavity of terminal bronchiole.

Embodiment 2

1. The Preparation of a Model with Emphysema Induced by TLR4 Mutant

Animals for experiment: C3H/HeN wild type mice on SPF level were purchased from Beijing Vitalriver Experimental Animals Limited Company. TLR4 mutant C3H/HeJ mice were purchased from Institute of model animals, Nanjing University.

Method: Fed the SPF mice and the TLR4 mutant mice in experimental animal center of Institute of pharmaceutics research, Chinese academy of medical sciences. Provide free diet under constant temperature and humidity. The mice were killed until they were 3 months old.

2. Treat Emphysema Induced by TLR4 Mutant in Mice by Rupatadine

Main agents and experimental animals: rupatadine, produced by Zhejiang Cifu pharmaceutical limited company. It was the API of rupatadine fumarate. The content of rupatadine was more than 99%. IL-17A used in positive control group was purchased from R&D Company.

Therapy: Grouping and feeding animal models with medicaments. The groups were shown in table 4:

TABLE 4

| Number | Group | The number of animals | Dosage and drug regimen | Route of administration | Solvent |
| --- | --- | --- | --- | --- | --- |
| A | Sham | 15 | Equivalent amount of solvent, lasting for 4 weeks after modeling, once a day | i.g. | PBS |
| B | Model | 20 | Equivalent amount of solvent, lasting for 4 weeks after modeling, once a day | i.g. | PBS |
| C | IL-17A | 20 | 1 g/kg IL-17A, lasting for 4 weeks after modeling, once a day | i.g. | PBS |
| D | Rupa | 20 | 6 mg/kg rupatadine, lasting for 4 weeks after modeling, once a day | i.g. | PBS |

Note:
Group A is sham-operation group (Sham). Group B is model group (Model). Group C is IL-17A treated group (IL-17A), and group D is rupatadine treated group (Rupa).

3. Pathological Evaluation of Mice with Emphysema Induced by TLR4 Mutant

HE staining method is also named Hematoxylin-Eosin staining Hematoxylin dye liquor is alkaline, and mainly colors intranuclear chromatin and intracytoplasmic ribosome into bluish violet; Eosin is acidic dye, and mainly colors the components in cytoplasm and extracellular matrix.

Figure 4:
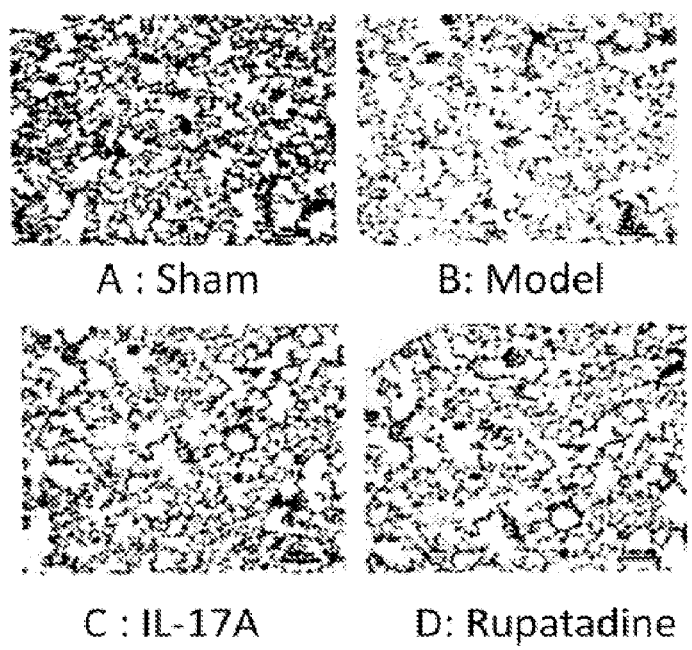
FIG. 4 shows pathological examination photos of lung tissue of sham-operation group, model group, positive control group and rupatadine treated group of TLR4-lacked emphysema mice in embodiment 2.

The lung tissues on the right lower lobe was cut, fixed by 4 wt % paraformaldehyde and then embedded by paraffin. The largest cross-section of the paraffin embedding the lung tissue was stained by HE staining method, and the result was shown in FIG. 4. FIG. 4 showed that the area of alveoli increased remarkably in mice with emphysema (FIG. 4B), and the far-end air cavity of terminal bronchiole was expanded, the normal lung tissue was destroyed, while positive control IL-17A (FIG. 4C) could effectively inhibit the further development of emphysema in mice. Rupatadine could effectively recover normal structure of alveoli (FIG. 4D), and decrease the expansion of far-end air cavity of terminal bronchiole.

Based on the analysis of embodiment 1 and 2, it can be concluded that rupatadine can effectively improve the pulmonary function and recover the basic physiological structure of lung in mice suffering COPD, and it can also alleviate the infiltration and expression of various inflammatory cells, and plays a role in adjusting body immune balance in chronic inflammatory pulmonary diseases, i.e. balancing immune reaction between Th1 and Th2.

Generally speaking, COPD patients in a stable phase have hyperfunctions of Th1 lymphocyte, while the balance between Th1/Th2 will shift to Th2 in an acute aggressive phase. Based on the above experiment results, it is reasonable to consider that rupatadine can resist inflammation and asthma, and adjust immune balance as well as convert COPD. As a result, rupatadine used in treating COPD will improve lung function, convert emphysema as well as alleviate the degree of inflammation and infiltration of various inflammatory cells.

What is claimed is:

1. A method of preventing or treating chronic obstructive bronchitis, obstructive emphysema or chronic obstructive pulmonary disease in a subject in need thereof, comprising: administering to the subject an effective amount of at least one active ingredient selected from the group consisting of rupatadine and a pharmaceutically acceptable derivative of rupatadine, the at least one active ingredient being provided in a pharmaceutical composition free of active ingredients other than rupatadine and its pharmaceutical acceptable derivative.

2. The method according to claim 1, wherein the pharmaceutically acceptable derivative is a pharmaceutically acceptable salt or ester of rupatadine.

3. The method according to claim 1, wherein the pharmaceutical composition comprises the at least one active ingredient and a pharmaceutically acceptable carrier.

4. The method according to claim 3, wherein the pharmaceutical composition comprises 0.1%-99% of the at least one active ingredient and 0.1%-99% of the carrier, the percentage is a mass percentage of each component to the total mass of the pharmaceutical composition.

5. The method according to claim 1, wherein the pharmaceutical composition is administered orally, intravenously, intramuscularly, intradermally or hypodermically.

6. The method according to claim 1, wherein the pharmaceutical composition is selected from an aqueous solution, a non-aqueous solution, and a suspension.

7. The method according to claim 3, wherein the pharmaceutical composition consists essentially of the pharmaceutically acceptable carrier and an effective amount of the at least one active ingredient.

8. The method according to claim 3, wherein the pharmaceutical composition consists of the pharmaceutically acceptable carrier and an effective amount of the at least one active ingredient.

9. The method according to claim 7, wherein the method consists essentially of administering to the subject the pharmaceutical composition.

10. The method according to claim 9, wherein the pharmaceutical composition consists of the pharmaceutically acceptable carrier and an effective amount of the at least one active ingredient.

11. The method according to claim 9, wherein the method consists of administering to the subject the pharmaceutical composition.

12. The method according to claim 11, wherein the pharmaceutical composition consists of the pharmaceutically acceptable carrier and an effective amount of the at least one active ingredient.

13. The method according to claim 1, wherein chronic obstructive bronchitis, obstructive emphysema or chronic obstructive pulmonary disease is treated in the method.

14. The method according to claim 3, wherein the method consists essentially of administering to the subject the pharmaceutical composition.

15. The method according to claim 3, wherein the method consists of administering to the subject the pharmaceutical composition.

* * * * *